United States Patent [19]

Castaneda

[11] Patent Number: 4,876,068
[45] Date of Patent: Oct. 24, 1989

[54] TEST KIT FOR COLORIMETRIC ANALYSIS

[75] Inventor: Henry B. Castaneda, Woodbridge, Va.

[73] Assignee: Chemetrics, Inc., Calverton, Va.

[21] Appl. No.: 318,903

[22] Filed: Mar. 3, 1989

[51] Int. Cl.$^4$ .................... G01N 31/02; G01N 31/22
[52] U.S. Cl. ......................................... 422/58; 422/61; 436/73; 436/77
[58] Field of Search ...................... 422/58, 61; 436/73, 436/77, 80, 81, 93, 169

[56] References Cited

U.S. PATENT DOCUMENTS

| | | | |
|---|---|---|---|
| 3,893,808 | 7/1975 | Cambell | 436/169 |
| 3,912,454 | 10/1975 | Snyder | 436/77 |
| 3,980,436 | 9/1976 | Greenfield et al. | 422/59 |
| 4,092,117 | 5/1978 | Byrne | 436/73 |
| 4,125,376 | 11/1978 | Razulis | 436/79 |
| 4,235,839 | 11/1980 | Vesterberg | 422/61 |
| 4,332,769 | 6/1982 | Rampy et al. | 422/61 |
| 4,409,182 | 10/1983 | Macklem | 422/61 |
| 4,434,235 | 2/1984 | Rabi et al. | 422/61 |
| 4,537,747 | 8/1985 | Castaneda | 422/100 |
| 4,770,853 | 9/1988 | Bernstein | 422/58 |
| 4,786,604 | 11/1988 | Michael | 436/77 |

FOREIGN PATENT DOCUMENTS 1542411 3/1979 United Kingdom .

OTHER PUBLICATIONS

Snyder, *Anal. Chem,* vol. 19 (9): 684-687 (Sep. 1947).
LaMotte Chemical Products Company, Information for Lead in Water Kit, Including Instruction Manual for the Octet Comparator; plus Two Photographs of the LaMotte Lead Kit.
Hach Chemical Company, Information for Hach Method of Analyzing for Lead Using Dithizone.

*Primary Examiner*—David L. Lacey
*Assistant Examiner*—Muir, Gregory
*Attorney, Agent, or Firm*—Timothy R. Kroboth

[57] ABSTRACT

A portable test kit for colorimetric analysis of trace levels of dithizone-complexing metal cations including lead, is provided. The test kit includes storage tubes each of which contains the reagents and apparatus required for a single test, and has sufficient volumetric capacity to serve as a vessel for the formation and extraction of colored, metal cation-dithizonate complex. Use of the test kit involves a novel and unique sampling technique for capturing a portion of a colored liquid within a container for viewing of the color. Also provided is an improved method for analyzing for trace levels of such metal cations.

5 Claims, 2 Drawing Sheets

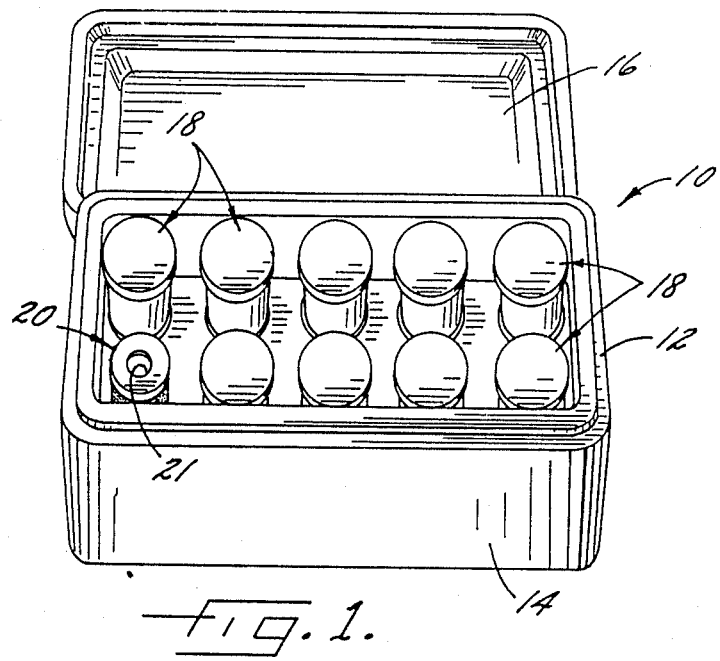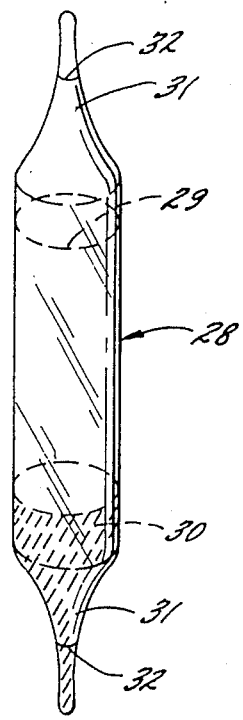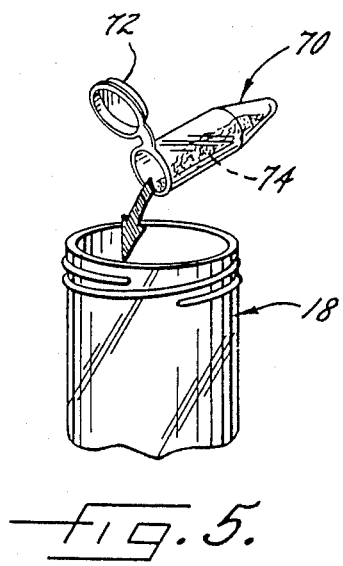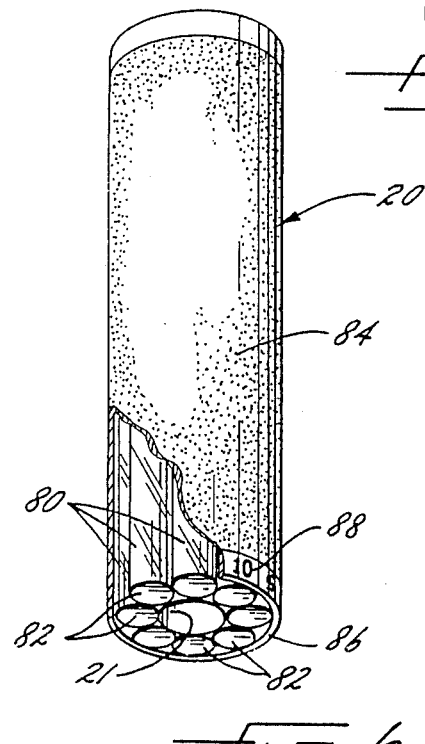

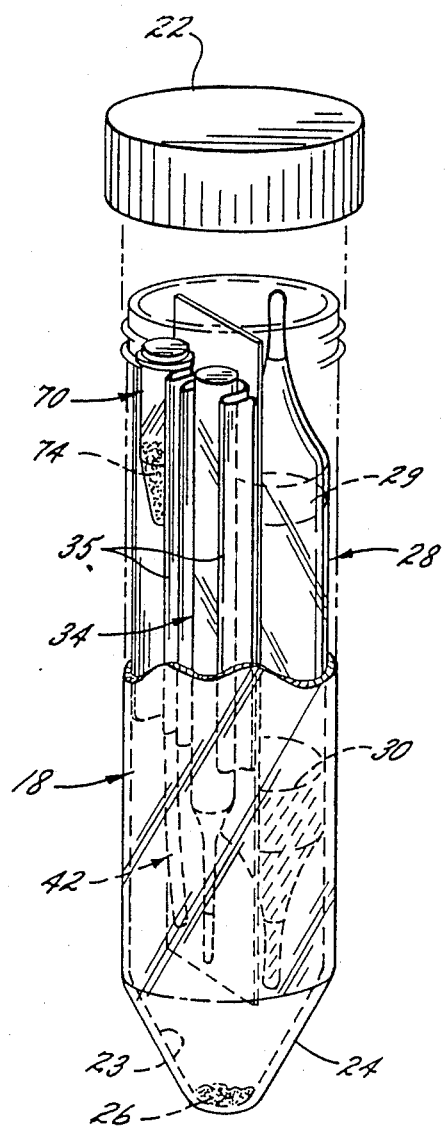

TEST KIT FOR COLORIMETRIC ANALYSIS

BACKGROUND OF THE INVENTION

This invention relates to the field of colorimetric analysis, more particularly to the analysis of trace levels of metals that form colored, extractable dithizonate complexes, such as heavy metals.

As illustrated by Snyder, *Anal. Chem.*, vol. 19 (9): 684–687 (September 1947), an improved dithizone method for colorimetric analysis of a lead-containing aqueous sample is known. In the method, dithizone is provided as a solution in chloroform, a water-immiscible extractant for the dithizonate complex; ammonium citrate, anhydrous sodium sulfite, potassium cyanide and ammonium hydroxide are employed as reagents; and the final extraction of the multiple extraction procedure is carried out at a pH of 11.5. Snyder uses an amount of dithizone that equals or exceeds more than 3000 $\mu$g, and evaluates color with a spectrophotometer.

Exposure to heavy metals continues to be a matter of concern. Exposure to lead in drinking water, regardless whether the lead is in source water or is from corrosion of plumbing materials, needs to be minimized.

Typically, analysis for heavy metals is carried out in certified laboratories. However, such an analysis does not provide an immediate answer, cannot be conducted on site, requires preservation of a sample for later analysis, requires a high level of technical expertise to conduct, and is expensive.

As illustrated by U.S. Pat. No. 4,770,853 to Bernstein, U.K. Pat. No. 1,542,411 of Carnie et al, and U.S. Pat. No. 3,980,436 to Greenfield et al, 4,786,604 to Michael, and 4,125,376 to Razulis, self-contained, portable devices are known for assays including colorimetric assays.

Bernstein, for example, describes a device for immunodiffusion assay that includes a sample collector, a tube with compartmentalized reagents and frangible seals, and a capture membrane disposed beneath the lower frangible seal to which sample and reagent are transferred from the sample collector by contact.

Carnie et al describe an analyzer for on the spot analysis of substances suspected of being explosives or narcotics. The analyzer includes a sample container connected to one end of a tube, a frangible ampoule containing a reagent, and a piston member which is inserted into the other tube end and employed to crush the ampoule.

The Greenfield et al patent pertains to a device including concentrically disposed tube and sleeve members providing an annular region between the members with a passage thereto that can be opened or closed. The outer tube has a conical bottom.

Michael describes a detector kit for testing for lead concentrations in excess of approximately 5 parts per million. The kit uses a sodium or potassium chromate solution.

The Razulis device is described as useful for colorimetrically detecting water pollutants including heavy metals, in concentrations measured in parts per million. The device is a test tube containing a foam cube impregnated with a detection chemical solution. A solution of dithizone in di-isobutyl phthalate, is utilized.

Also known is a test kit for lead in water, that includes a stock solution of dithizone in carbon tetrachloride, a water-immiscible organic extractant for lead dithizonate, stored with an aqueous preservative solution. The aqueous solution forms an upper layer and the organic solution forms a lower layer of a biphasic liquid. The test kit further includes a plastic squeeze bottle containing an alkaline solution of cyanide as a stock solution, bottles of pH-adjusting solutions, a pipette having a squeeze bulb, a test tube marked with a fill line and having a stopper, a wash bottle for providing wash water, and a comparator. The kit lacks a deactivator for unreacted cyanide.

In use, the pH of a water sample is determined and adjusted; the pipette tip is inserted into the lower layer of the biphasic liquid, the pipette is filled with an amount of the dithizone stock solution appropriate for a single test (equivalent to about 600 $\mu$g/60 ml), and the contents of the pipette are transferred to the test tube; and a specified number of drops of the cyanide stock solution for a single test, are squeezed from the plastic bottle into the test tube. Thereafter, the pH-adjusted water sample is added to the test tube until the fill line is reached; the test tube is capped and shaken vigorously, and the contents allowed to separate into upper and lower layers; and the test tube is inserted into the comparator for viewing through tube side walls. The pipette and test tube are washed for reuse in a subsequent test.

Accordingly, there is a need for an improved portable test kit for colorimetric analysis of trace levels of heavy metals in an aqueous sample. The kit should be simple to use. The test kit should provide results quickly and be cost-effective. In those cases where a sample is found to contain a level of metal of concern, the sample could be preserved and submitted to a certified lab.

Such a kit should also be safe to dispose of, and beneficially would provide an improved method for colorimetrically analyzing for trace levels of heavy metals. In particular, there is a need for a portable test kit sensitive for lead levels in the range of 5 to 10 ppb. By the term, "ppb" is meant $\mu$g per liter.

SUMMARY OF THE INVENTION

It is accordingly an object of the present invention to provide an improved portable test kit for colorimetric analysis of trace levels of heavy metals in an aqueous sample.

It is a further object to provide a kit that is simple to use.

It is a still further object to provide a test kit that rapidly determines heavy metal content at a low cost per analysis.

It is an additional object to provide a test kit that is also safe to dispose of.

It is an even additional object to provide an improved method for colorimetrically analyzing for trace levels of heavy metals.

It is also an object of the present invention to provide a portable test kit sensitive for lead levels in the range of 5 to 10 ppb.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided a portable test kit useful in the field for colorimetric analysis of trace levels of certain metals in an aqueous sample. Such metals form colored, extractable dithizonate complexes. The test kit includes a plurality of storage tubes each provided with a lid and having a conically-shaped end. A unit dose amount of dithizone is disposed in solid form on an inner wall of the conically-shaped end of each tube.

Each storage tube further contains the remaining reagents, each in an amount appropriate for a single test, a closed container, a sealed, evacuated container, and a hollow tube. Preferably, for a lead test, each storage tube also contains a reagent for destroying any unreacted cyanide.

The closed container contains in biphasic liquid form, an extractant for a metal cation-dithizonate complex and test reagents. The extractant is of greater density than water. The sealed, evacuated container is for capturing a portion of a layer formed by dithizonate complex-containing extractant, and for viewing the color of the captured layer portion.

The hollow tube has an end adapted to form an air-tight sealing relationship with the evacuated container, and, when the evacuated container and the extending tube are in the air-tight sealing relationship, has an open end but is otherwise closed to the ambient atmosphere. Preferably, the tube is of sufficient length for avoiding undesirable aspiration of aqueous contaminant and for controlling the high fluid flow that accompanies accessing the negative pressure of the evacuated container.

Each storage tube is of sufficient volumetric size to contain at the same time the extractant and a metal containing, aqueous sample of greater volume than the extractant. In this way, a storage tube serves as a vessel for the formation and extraction of the dithizonate complex.

The test kit also includes a comparator for providing comparison of the color of the captured layer portion, with color standards.

Also provided by the present invention is a method useful in the field for the colorimetric analysis of trace levels of such metals in an aqueous sample. The method includes removing the metal from a relatively larger volume of an aqueous sample, and concentrating the metal in a relatively smaller volume of an extractant for a metal cation-dithizonate complex. The extractant is of greater density than water. Thereafter, the resulting biphasic mixture is allowed to separate into an upper aqueous layer and a colored, lower organic layer.

Then, an open end of a hollow tubular body is passed through the upper aqueous layer into the lower organic layer without contamination of the hollow tubular body interior by the aqueous layer. The hollow tubular body has another end in an air-tight sealing relationship with a sealed, evacuated container and is otherwise closed to the ambient atmosphere.

The negative pressure within the evacuated container is accessed, and without aspirating aqueous contaminant, a portion of the lower organic layer is drawn by the negative pressure, through the open end of the hollow tubular body into the container. The color of the organic liquid captured within the container, the captured liquid being free of aqueous contaminant, is then compared to color standards, preferably by viewing through a longitudinal liquid pathlength.

In the drawing and in the detailed description of the invention that follows, there is shown and essentially described only a preferred embodiment of this invention, simply by way of illustration of the best mode contemplated by me of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWINGS

Reference is now made to the accompanying drawing, which forms a part of the specification of the present invention, and which depicts a preferred embodiment of a test kit in accordance with the present invention.

FIG. 1 is a perspective view of a preferred embodiment of a portable test kit in accordance with the present invention, showing the test kit with the upper container lid removed;

FIG. 2 is an enlarged view of a tube including its contents, the tube having been removed from the kit container shown in FIG. 1;

FIG. 3 is a view of a double-tipped, sealed container, shown vertically oriented, which was stored in the tube of FIG. 2;

FIG. 4 is an enlarged view of a tube 18 containing upper and lower liquid layers, with an evacuated container and a tip-extending tube assembled together, shown prior to snapping the tip of the container;

FIG. 5 is a view showing the contents of a micro test tube, which was also stored in he tube of FIG. 2, being added to the tube; and FIG. 6 is an enlarged perspective view of a comparator, the comparator having been removed from the kit container of FIG. 1.

DETAILED DESCRIPTION OF THE INVENTION

The present invention is a portable test kit useful in the field for colorimetric analysis of trace levels of certain metals in an aqueous sample such as drinking water. The metals must form a dithizonate complex. Exemplary heavy metals include bismuth, cadmium, cobalt, copper, lead, mercury, nickel, palladium and silver.

The test kit is self-contained and compact. The kit utilizes chemistry of the dithizone method, similar to that of the Snyder article, discussed earlier. Beneficially, the kit uses preformulated reagents, premeasured in unit doses to minimize operator error. Nevertheless, the kit is best suited for use by a skilled technician, although non-technical individuals such as homeowners could safely use the kit with accurate results.

The results are quantified by comparing the color intensity of a colored dithizonate complex-containing extractant with color standards. Test sensitivity is enhanced by capturing the colored extractant inside a cylindrical container, and viewing the color through a longitudinal liquid pathlength.

The compact kit is well suited for screening for trace levels of lead, with accuracy in the range of about 0 to 100 ppb lead, and in a preferred embodiment with accuracy in the range of about 0 to 50 ppb, with sensitivity for lead levels of about 5 to 10 ppb. For ease of understanding, the description that follows, is particularly directed to a test kit for analyzing for trace levels of lead.

Referring to FIG. 1, a portable test kit 10, in accordance with the present invention, includes a container 12 having a base 14 and a cover 16. Inside the container, tubes 18 and a comparator 20 having a cylindrical slot 21 are stored. The tubes, which are advantageously disposable, provide storage for the reagents and other apparatus needed.

With reference now to FIG. 2, each storage tube 18 is provided with a removable lid 22 and has a conically-shaped end 24. Conveniently, the tubes are made of plastic and provided with volume-indicating marks 25, shown in FIG. 4. It is highly preferable that the tubes be transparent.

Disposed on an inner wall 23 of conically-shaped end 24 of each storage tube is a premeasured amount of dithizone 26 in solid form, typically solid thin film form. Conveniently, the dithizone is deposited in this form by addition to the tube of an appropriate volume of a freshly made, dithizone-containing stock solution, followed by solvent evaporation. Providing the dithizone in solid form avoids the stability problems of a dithizone stock solution, and thereby assists the use of a low dosage of dithizone.

The amount of dithizone is selected based upon a variety of parameters including the sample volume to be extracted and the sensitivity desired for the test, but in any event is a unit dose amount, that is, the amount for a single test. Unlike the Snyder method, in testing for lead, the present invention utilizes an amount of dithizone equivalent to less than about 1500 $\mu$g per approximately 60 ml of sample, and for a sensitivity of about 0–50 ppb lead, less than about 1000 $\mu$g per about 60 ml of sample.

A beneficial amount of dithizone is about 150–750 $\mu$g for a sensitivity of about 0–50 ppb or 0–100 ppb lead, with a sample size of about 60 ml. A preferred amount of about 450 $\mu$g is significantly less than the amount used by Snyder, and provides a visually discernible color intensity difference for a lead content in the range of about 5–10 ppb.

Within each storage tube 18 is a sealed container 28, best seen in FIG. 3, containing a biphasic liquid having an aqueous phase 29, and a small volume of an organic phase 30 of greater density than water. Advantageously, sealed container 28, which is preferably made of glass and is to be discarded after use, has ends drawn out in slender, thin-walled, frangible tips 31, which preferably have score marks 32 for easy breaking of the tips. Double-tipped, sealed containers are commercially known.

An extractant for a metal cation-dithizonate complex forms organic phase 30, and aqueous phase 29 contains the remaining reagents for a single test. The volume of the extractant and the amounts of the remaining reagents are appropriate for a single test.

It is preferred, for a lead test, that the aqueous phase is an ammoniacal citrate-cyanide reducing solution, and that it accordingly contains ammonium citrate and cyanide ion; and preferably the water-immiscible organic phase is carbon tetrachloride. The ammoniacal citratecyanide reducing solution contains dibasic ammonium citrate, anhydrous sodium sulfite, hydroxyamine hydrochloride, potassium cyanide and concentrated ammonium hydroxide. This solution is formulated to compensate for common interfering agents, such as other metals, and provides an appropriate pH, for a lead test, ranging from greater than about 10 to less than about 11.5, preferably about 10.5, for a carbon tetrachloride extraction.

In the preferred lead test method, lead is reacted with the ammoniacal citrate-cyanide reducing solution, and is then extracted with dithizone into a solution of carbon tetrachloride. The reaction product is the pink colored, lead dithizonate. The intensity of the color is directly proportional to the concentration of dissolved lead in the sample. Unreacted dithizone, due to the absence of lead, would provide a yellow solution.

For a lead test using about 450 $\mu$g of dithizone, an about 15 ml sealed container 28 having a length of about 120 mm and a diameter of about 20 mm, is conveniently used to store about 11.25 ml of the reducing solution and about 3 ml of carbon tetrachloride. For such a test, the ammoniacal citrate-cyanide reducing solution beneficially contains about 1.2 g of dibasic ammonium citrate, about 70 mg of anhydrous sodium sulfite, about 40 mg of hydroxylamine hydrochloride, about 150 mg of potassium cyanide, and about 9.0 ml of concentrated ammonium hydroxide.

For such a test, a preferred aqueous sample volume is about 60 ml. Such a sample volume provides a preferred ratio, an about 20:1 ratio, of sample (about 60 ml) to extractant (about 3 ml). For test sensitivity at levels of about 5 to 10 ppb lead, the sample to extractant volume should exceed an about 15:1 ratio. An even greater ratio than a 20:1 ratio could, of course, be employed, but an about 20:1 ratio provides a clearly discernible color intensity difference between 0 ppb lead, 5 ppb lead and 10 ppb lead. A ratio of about 10:1 of sample to extractant volume is suitable for sensitivity of about 0–100 ppb lead.

Again with reference to FIG. 2, also within each storage tube 18 is a sealed container 34, partially or completely evacuated of air, which is separated by a separator 35, from container 28. Evacuated container 34, which is preferably made of glass and is to be disposed of after the test, is typically empty, that is, it contains no accessory reagent.

The evacuated container, best seen in FIG. 4, preferably is cylindrically shaped with a flat end 36 and has an end drawn out in a slender, thin-walled, frangible tip 38, which preferably has a score mark 40. The evacuated container is used to capture a portion of the small volume of dithizonate complex-containing extractant for accurate, comparative viewing of the color.

With continued reference to FIG. 2, also within each storage tube 18 is a tube 42, best seen in FIG. 4, for extending tip 38 of container 34. An end 44 of tip extending tube 42 has an internal diameter relative to the outside diameter of the slender ampoule tip that enables end 44 to fit over a portion 46 of the slender tip and form an air-tight seal above, with reference to FIG. 4, score mark 40. A similarly constructed, commercially known device containing a ball-valve in the tube thereof, and another commercially known device including a two-way vent port in a tube thereof, are respectively illustrated by U.S. Pat. 4,332,769 to Rampy et al, and U.S. 4,537,747.

As indicated in FIG. 4, a portion of the extractant is selectively withdrawn from a biphasic mixture having an upper aqueous layer 50 and a lower extractant layer 52. It is important that only dithizonate complex containing extractant, and not any aqueous contaminant, be drawn into container 34. Therefore, unlike the device of U.S. 4,537,747, only a tube end 54 is open to the ambient atmosphere when the air-tight seal has been formed between extending tube 42 and sealed container 34. In this way, a positive pressure is maintained that prevents aqueous contaminant from entering the tube, as tube end 54 is passed through the upper aqueous layer into the lower extractant layer.

Without the extending tube, movement of container 34 in snapping tip 38, could disadvantageously result in the shortened tip accidentally entering the aqueous layer. Also, because tip 38 is shortened when snapped, the shortened tip would be closer to the aqueous layer and be further removed from a bottom 56 of conically-shaped end 24 of tube 18.

The extending tube, which advantageously is disposable, is made of a pressure-deformable material that is preferably heat-shrinkable and also transparent. Pressure-deformability enables the frangible tip of evacuated container 34 to be broken readily at score mark 40 by pressure exerted through a wall 48 of the extending tube. Conventional pressure-deformable, heat-shrinkable, transparent polyolefin tubing may be beneficially used as the extending tube.

Referring to FIG. 4, the length of tip-extending tube 42 is preferably sufficient for open end 54, when end 44 of the extending tube is in an air-tight sealing relationship with the evacuated container, to touch and be in contact with bottom 56 of tube 18. Such a length permits negative pressure to be applied at or near bottom 56.

Combined with the conical shape of end 24, use of an extending tube of such length assists the selective capture of a portion of lower organic layer 52 formed by the small volume of dithizonate complex-containing extractant without detrimental aspiration of upper aqueous layer 50. Furthermore, because open end 54 of an extending tube of such length is remote from the source of the negative pressure, the high fluid flow that accompanies accessing the negative pressure, is controllably utilized such that dithizonate complex-containing extractant is captured but aspiration of aqueous contaminant is avoided. For a 100 ml tube 18 of about 130 mm length and about 30 mm diameter, an advantageous length for the extending tube is about 85 mm.

When connected to container 34, an extending tube of such length and an internal diameter of about 2 mm has a volumetric capacity of about 0.3 ml. As can be understood, the air contained in the extending tube is drawn into container 34. As a result, there will be an air bubble in the colored liquid in the container. If desired, the air bubble can be reduced, say about one-third or so, in size, by using a heat-shrunk extending tube of about one-third the volumetric capacity, that is, about 0.1 ml.

The air in the extending tube results in less than a 100% fill of container 34 with liquid. A preferred fill volume for evacuated container 34 is less than the combined volume of the extractant, and of the air in the extending tube. In this way, undesirable aspiration of aqueous contaminant during extractant capture, is minimized. A fill volume of about 1.5-2.0 ml, preferably about 1.8 ml, is advantageous when about 3 ml of extractant is used.

Such a fill volume may be provided by a container 34 having a length including the frangible tip of about 9095 mm, preferably 92.5 mm, and a diameter of about 7 mm. When 0.3 ml of air is drawn into a container of about 1.8 ml fill volume, about 1.5 ml of extractant is captured, and the height of the captured liquid in a container 34 of such dimensions will be about 60 mm. Thus, a long longitudinal liquid pathlength for viewing the extractant color is provided.

With continued reference to FIG. 2, preferably for a lead test, within each storage tube 18 is a micro test tube 70, best seen in FIG. 5, which has a lift-off cap 72 and is advantageously disposable. The micro test tube, which is preferably made of plastic, contains a reagent 74 for destroying any unreacted cyanide, after a lead test is completed. This feature makes the chemicals used in a lead test, safe to dispose of.

A suitable reagent for destroying unreacted cyanide is ferrous ammonium sulfate in solid form. When about 0.15 g of potassium cyanide is used, about 0.25 g of ferrous ammonium sulfate may be satisfactorily employed for this purpose.

The volumetric size of tube 18 must further provide the capacity to contain at the same time the small volume of extractant and an aqueous sample of considerably greater volume, say on the order of about ten to twenty times greater, than the extractant, and thereby serve as a vessel for the formation and extraction of dithizonate complex. For a test using a unit dose of dithizone in the amount of about 450 ug and about 3 ml of carbon tetrachloride, a sample size of about 60 ml is advantageous, with a suitable volumetric size being about 100 ml for tube 18.

Referring now to FIG. 6, comparator 20 is also provided by the test kit. The comparator, which is commercially known, is advantageously made of several sealed, cylindrical containers 80, each containing a stable liquid color standard and having a flat bottom 82, disposed in a cylindrically-shaped container 84 also having a flat bottom 86. For a test with a sensitivity of about 0-50 ppb, liquid color standards for 0, 5, 10, 15, 20, 30, 40 and 50 ppb, would preferably be disposed in container 84, with the ppb shown by numbers 88. Centrally disposed in container 84 is cylindrical slot 21, also shown in FIG. 1, into which container 34 is to be inserted for comparative viewing of the extractant color though the longitudinal liquid pathlength.

Other types of comparators could be used with the test kit. For instance, a color chart could be employed. Comparator 20 is the preferred comparator.

As can be understood, other than comparator 20, the test kit of the present invention is advantageously disposable. Accordingly, after running a test, the used test kit components are returned to the storage tube, which contains residual liquid, and the test tube is recapped and discarded with its contents. Therefore, clean-up of dirty equipment and the possibility of a false result with a subsequent test sample due to contaminated equipment, are avoided. This feature is important in analyzing for trace quantities of metals using a test based upon high sensitivity.

In use, double-tipped container 28 containing an organic extractant of greater density than water, sealed evacuated container 34, valveless, tip-extending tube 42, which is open from one end to the other, and sealed micro test tube 70 are removed from storage tube 18. The liquid contents of the double-tipped, sealed container are added to tube 18 by snapping one tip end and then the other. Prior to or after adding those liquid contents, the sample to be analyzed is poured into tube 18. The sample is beneficially of substantially greater volume, say on the order of about ten to twenty times greater volume, than the volume of the extractant.

The resulting mixture is shaken to effect formation of colored, extractable, metal cation-dithizonate complex and extraction thereof by the extractant. The aqueous and organic phases are allowed to separate into upper and lower layers, respectively. As a result, the metal is removed from a large volume of sample and concentrated in a small volume of an extractant.

End 44 of tip-extending tube 42 is fit over tip 38 of evacuated container 34 to form an air-tight seal, and open end 54 of the extending tube is thereafter passed through upper aqueous layer 50 into colored, lower organic layer 52 without contamination of interior 60 of tube 42 by the aqueous layer. Preferably with the open end of the extending tube resting against bottom 56 of the tube 18, frangible tip 38 of the evacuated container is snapped at score mark 40 by pushing the tip against a side wall 62 of tube 18; as a result, a portion of the lower organic layer is drawn by negative pressure through the open end of the extending tube into container 34. The colored liquid drawn into container 34 is free of aqueous contaminant.

Thereafter, container 34 is inserted into cylindrical slot 21 of the comparator, and the color of the liquid within that container is compared with the colored liquid standards of the comparator. The liquids are advantageously viewed through the longitudinal pathlength. The analysis time per test is approximately 1–2 minutes, and the cost per test is substantially less than a laboratory test.

In this way, the kit provides a method for concentrating a dithizonate-complexing metal into a small volume of an extractant, transferring a portion of the colored, dithizonate complex-containing extractant into an elongated container, and analyzing the color of the extractant in the elongated container.

As explained, each compact test kit is selfcontained and, as shown in FIG. 1, advantageously includes everything required to perform up to nine tests. As can be understood, the kit is easy to use and provides an accurate, on-site method for analyzing for trace levels of inorganic lead, with sensitivity in the range of about 0 to 50 or 0100 ppb lead, and in a highly preferred embodiment with distinguishable color intensity at 0 ppb, 5 ppb and 10 ppb lead.

Having described the invention in detail and by reference to a preferred embodiment thereof, it will be apparent that modifications and variations are possible without departing from the scope of the invention defined in the appended claims. Several changes or modifications have been briefly mentioned for purposes of illustration.

I claim:

1. A portable test kit useful in the field for colorimetric analysis of trace levels of a dithizonate complexing metal cation in a aqueous sample, said kit comprising
   at least one storage tube and lid member assembly, said at least one assembly comprising a storage tube having a conically-shaped end, and being of sufficient volumetric size to serve as a vessel for formation and extraction of an extractable, metal cation-dithizonate complex, and said at least one storage tube and lid member assembly containing
   a unit dose amount of dithizone in solid form
   a closed container containing in biphasic liquid form, an organic extractant for said metal cation-dithizonate complex, and an aqueous phase containing accessory test reagents for providing appropriate selectivity, said extractant being of greater density than water and being provided in a volume that provides an at least about 10:1 volume ratio of said aqueous sample to said organic extractant;
   a sealed, evacuated container means for capturing a portion of a layer formed by colored, dithizonate complex-containing, organic extractant, upon accessing the vacuum in said evacuated container means;
   a hollow tubular body having an end constructed so as to form an air-tight sealing relationship with said evacuated container means and, when said evacuated container means and said hollow tubular body are in said air-tight sealing relationship, said combination thereof being open to the ambient atmosphere only at another end of said hollow tubular body; and
   means for providing analysis of the color of said captured layer portion.

2. The portable test kit of claim 1, wherein said hollow tubular body is of sufficient length to touch and be in contact with a bottom portion of the conically shaped end of said storage tube.

3. The portable test kit of claim 1, wherein said dithizonate-complexing metal cation is lead.

4. The portable test kit of claim 3, wherein said aqueous phase comprises ionic cyanide, and wherein said at least one storage tube and lid member assembly further contains a reagent for destroying any unreacted cyanide, in an amount sufficient for destroying unreacted cyanide.

5. The portable test kit of claim 4, wherein said reagent for destroying any unreacted cyanide is ferrous ammonium sulfate.

* * * * *